(12) United States Patent
Schwartz et al.

(10) Patent No.: US 7,555,348 B1
(45) Date of Patent: Jun. 30, 2009

(54) REMOTE TRANSTELEPHONIC MONITOR USER INTERFACE

(75) Inventors: Allan R. Schwartz, Moorpark, CA (US); Monique Prue, Los Angeles, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 472 days.

(21) Appl. No.: 11/243,413

(22) Filed: Oct. 3, 2005

Related U.S. Application Data (60) Provisional application No. 60/629,850, filed on Nov. 19, 2004.

(51) Int. Cl.
*A61N 1/00* (2006.01)
(52) U.S. Cl. .................................................. 607/60
(58) Field of Classification Search ............... 607/59, 607/60
See application file for complete search history.

(56) References Cited

U.S. PATENT DOCUMENTS

| | | | | |
|---|---|---|---|---|
| 4,281,664 A | * | 8/1981 | Duggan .................. | 600/508 |
| 4,361,153 A | * | 11/1982 | Slocum et al. ........... | 607/32 |
| 4,586,508 A | * | 5/1986 | Batina et al. ............ | 607/32 |
| 5,941,829 A | | 8/1999 | Saltzstein et al. ......... | 600/509 |
| 6,083,248 A | | 7/2000 | Thompson ............... | 607/30 |
| 6,275,737 B1 | * | 8/2001 | Mann .................... | 607/61 |
| 6,398,727 B1 | | 6/2002 | Bui et al. ............... | 600/300 |
| 6,558,321 B1 | | 5/2003 | Burd et al. .............. | 600/300 |
| 6,738,671 B2 | | 5/2004 | Christophersom et al. ... | 607/60 |
| 2001/0039504 A1 | | 11/2001 | Linberg et al. ........... | 705/3 |
| 2002/0065682 A1 | | 5/2002 | Goldenberg ............. | 705/2 |
| 2006/0161213 A1 | | 7/2006 | Patel | |
| 2006/0161214 A1 | | 7/2006 | Patel | |

FOREIGN PATENT DOCUMENTS

| | | |
|---|---|---|
| EP | 1168960 B1 | 8/2001 |
| WO | WO 01/56467 A1 | 8/2001 |
| WO | WO 03/020127 A1 | 3/2003 |

* cited by examiner

*Primary Examiner*—Mark W Bockelman
*Assistant Examiner*—Eric D Bertram
(74) *Attorney, Agent, or Firm*—Steven M. Mitchell (57) ABSTRACT

Patients fitted with an implantable medical device (IMD) must typically return to their medical providers for follow-up sessions where the medical provider retrieves data from the patient's IMD for analysis. A remote monitoring device is described to allow patients to complete a follow-up session from the comfort of their own home or from some other remote location. Specifically, a user interface employing various audio signals, light indicators, and tactile features is described to aid patients with hearing and/or visual disabilities during the remote follow-up session. Different light indicator states are used to aid hearing impaired patients. Different audio sound states are used to aid visually impaired patients. Furthermore, tactile features are used to aid hearing and/or visually impaired patients.

14 Claims, 6 Drawing Sheets

REMOTE TRANSTELEPHONIC MONITOR USER INTERFACE

CROSS REFERENCE TO RELATED APPLICATIONS

This application claims priority under 35 U.S.C. §119(e) to commonly owned U.S. Provisional Patent Application No. 60/629,850, filed Nov. 19, 2004.

BACKGROUND OF THE INVENTION

1. Field of the Invention

The present invention relates generally to systems for remotely monitoring patients fitted with an implantable medical device (IMD).

2. Background Art

Implantable medical devices (IMDs) fitted within a patient are often capable of transmitting data to sources outside the patient to relay information about the device and/or information the device has obtained about the patient. Typically, patients fitted with an IMD make follow-up visits to their medical provider so that information from the IMD can be obtained for analysis.

Rather than returning to the medical provider for these follow-up sessions, a system that allows patients to obtain data from their IMD and remotely transmit the data to their medical provider would allow the patients to complete these follow-up sessions from the comfort of their own home or from other remote locations. Such systems need to be accessible to older patients who may have hearing and/or visual disabilities.

What is needed is a system for remotely monitoring patients fitted with an IMD that includes a simple user interface for patients who may be hearing and/or visually impaired.

BRIEF SUMMARY OF THE INVENTION

A remote monitoring device is described that allows a patient fitted with an IMD to complete follow-up sessions from their own home or from other remote locations. The remote monitoring device includes a wand that can be placed near the patient's IMD to retrieve data from the IMD, a transceiver to relay the retrieved data to the medical provider, a speakerphone to communicate with the medical provider during the follow-up session, and light and/or audio indicators.

To aid patients with hearing and/or visual disabilities, a user interface utilizing different audio signals, light indicators, and tactile features is employed by the remote monitoring device. Different light indicator states are used to inform hearing impaired patients of the progress of the follow-up session. Different audio sound states are used to inform visually impaired patients of the progress of the follow-up session. Furthermore, tactile features are used to aid hearing and/or visually impaired patients.

Further embodiments, features, and advantages of the present invention, as well as the structure and operation of the various embodiments of the present invention, are described in detail below with reference to the accompanying drawings.

BRIEF DESCRIPTION OF THE DRAWINGS/FIGURES

The accompanying drawings, which are incorporated herein and form a part of the specification, illustrate the present invention and, together with the description, further serve to explain the principles of the invention and to enable a person skilled in the pertinent art to make and use the invention.

The present invention will be described with reference to the accompanying drawings. The drawing in which an element first appears is typically indicated by the leftmost digit(s) in the corresponding reference number.

DETAILED DESCRIPTION OF THE INVENTION

Implantable medical devices include, for example and without limitation, pacemakers, pulse generators, and cardioverter defibrillators. The term "implantable medical device," or simply "IMD," is used herein to refer to, non-exclusively and without limitation, any pacemaker, pulse generator, or cardioverter defibrillator. As used herein, the term IMD also includes other implantable devices such as artificial organs, insulin pumps, drug delivery devices, and other implanted devices for sensing physiologic parameters or delivering electrical or pharmaceutical therapy to the body.

For examples of IMDs, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734, entitled "Efficient Generation of Sensing Signals in an Implantable Medical Device such as a Pacemaker or ICD" (McClure et al.), which patents are hereby incorporated herein by reference.

An IMD is generally capable of transmitting information obtained during its operation to external devices. The information retrieved from the IMD can be analyzed by the patient's medical provider to treat the patient and to ensure that the IMD is functioning properly. IMDs may utilize various mechanisms to transmit such information to external devices as would be appreciated by persons skilled in the relevant art. Such mechanisms may include, for example, the use of an RF transmitter. Typically, the information from the IMD is retrieved at a doctor's office, clinician's office, or follow-up center.

Rather than requiring a patient to physically visit his or her medical provider to retrieve the information from his or her IMD, a remote monitoring system can be utilized to allow a doctor or clinician to remotely obtain the desired information from the patient's IMD.

Figure 1:
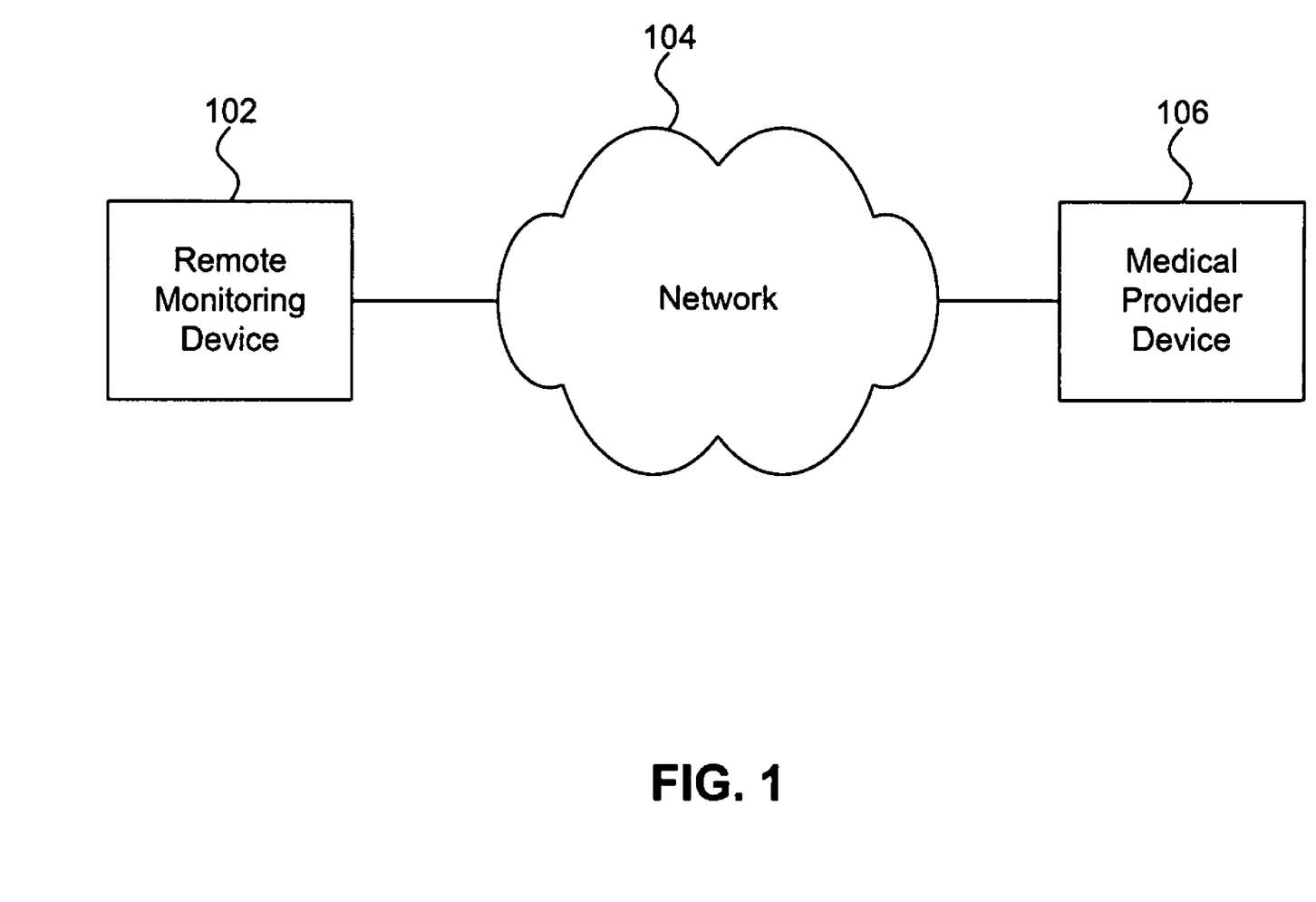
FIG. 1 is a block diagram of an exemplary system for remote monitoring of implantable medical devices.

FIG. 1 is a block diagram of an exemplary system for remote monitoring of an IMD. As shown in FIG. 1, a patient with an IMD (not shown) can utilize a remote monitoring device 102 in the comfort of their own home or at a location separate from the medical provider to allow the medical provider to obtain information from the IMD. The information can be transmitted over a network 104 to a receiving device 106 at the medical provider's site. Network 104 may be a public telephone system, Internet, or other transmission system as would be appreciated by persons skilled in the relevant art. The receiving device 106 may be a computer or any other device capable of receiving the transmitted information as would be appreciated by persons skilled in the relevant art.

Figure 2A:
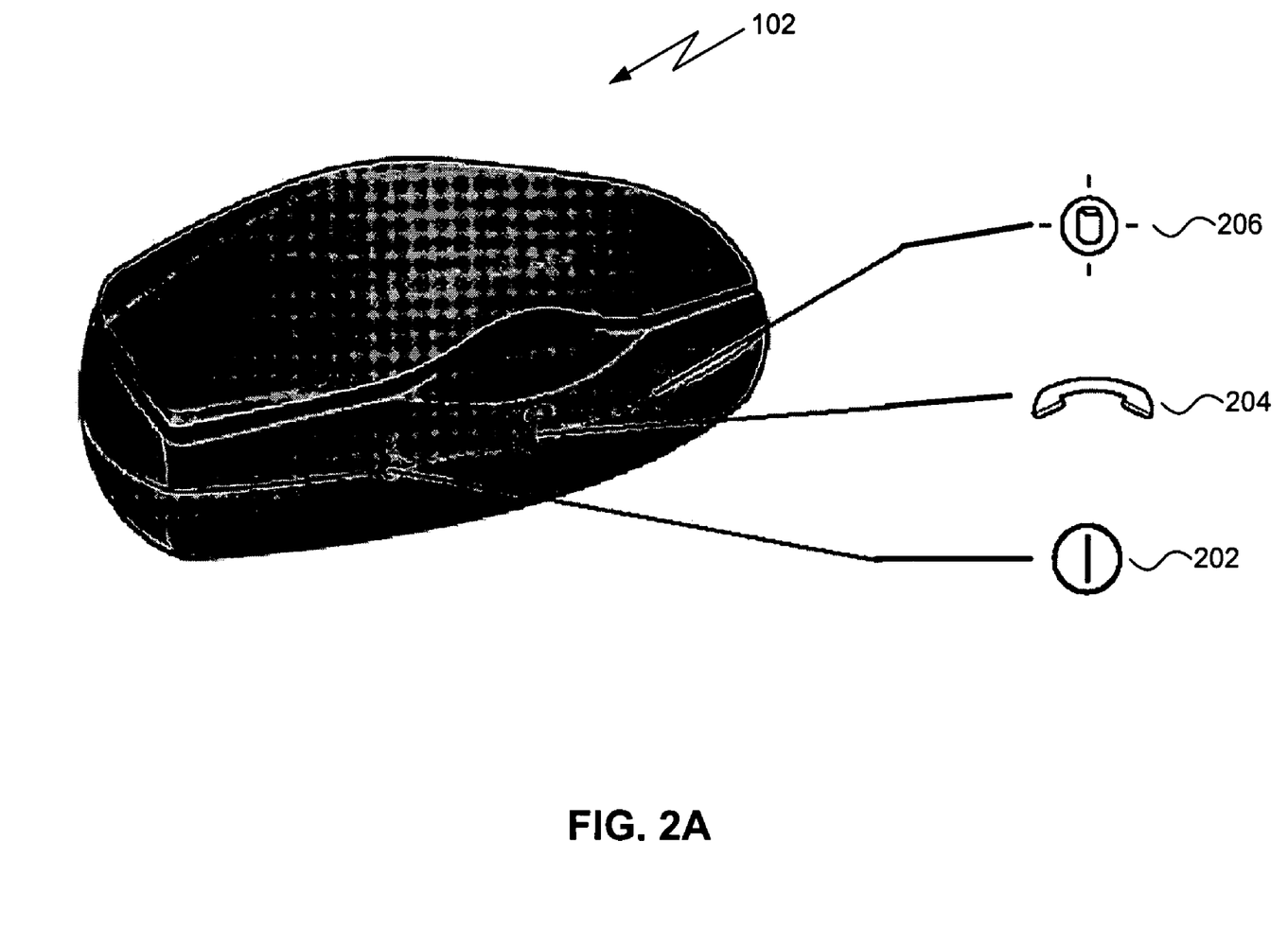
FIG. 2A is an illustration of a first view of an exemplary remote monitoring device.
Figure 2B:
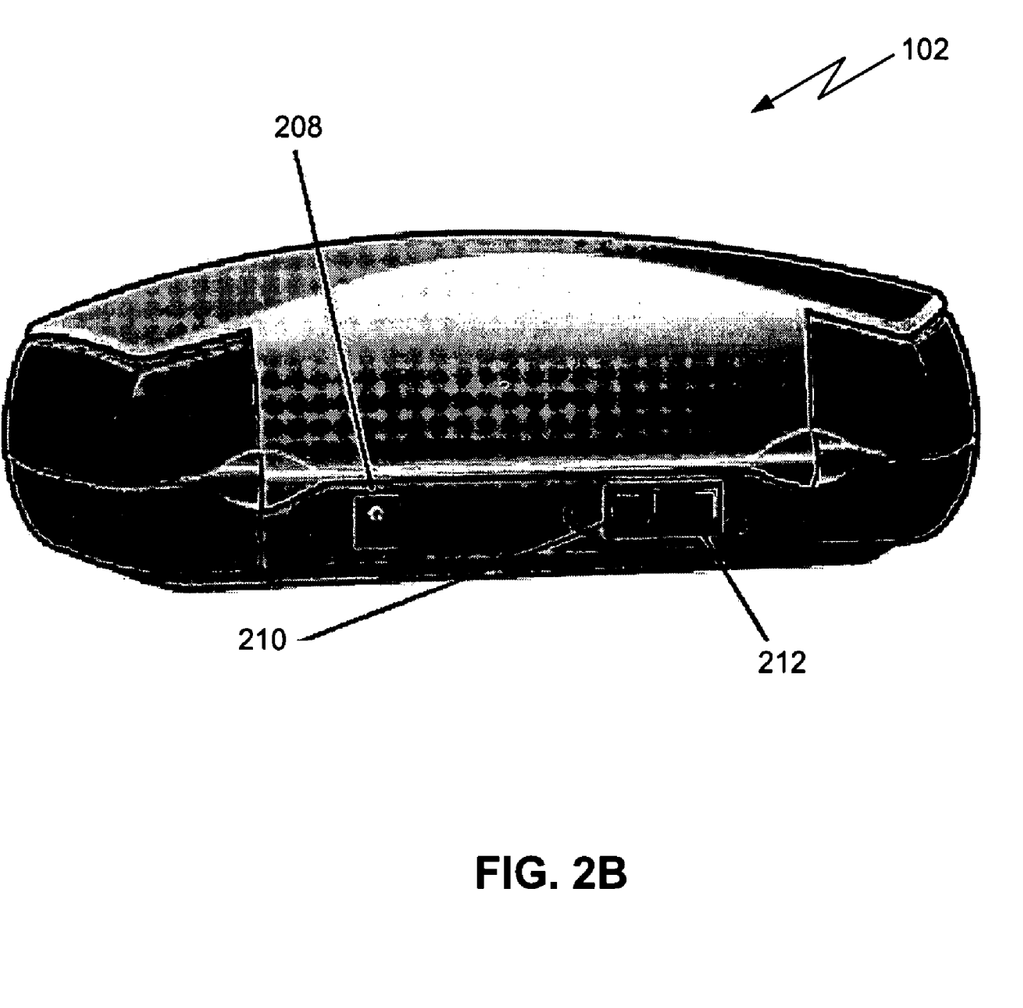
FIG. 2B is an illustration of a second view of the exemplary remote monitoring device.
Figure 2C:
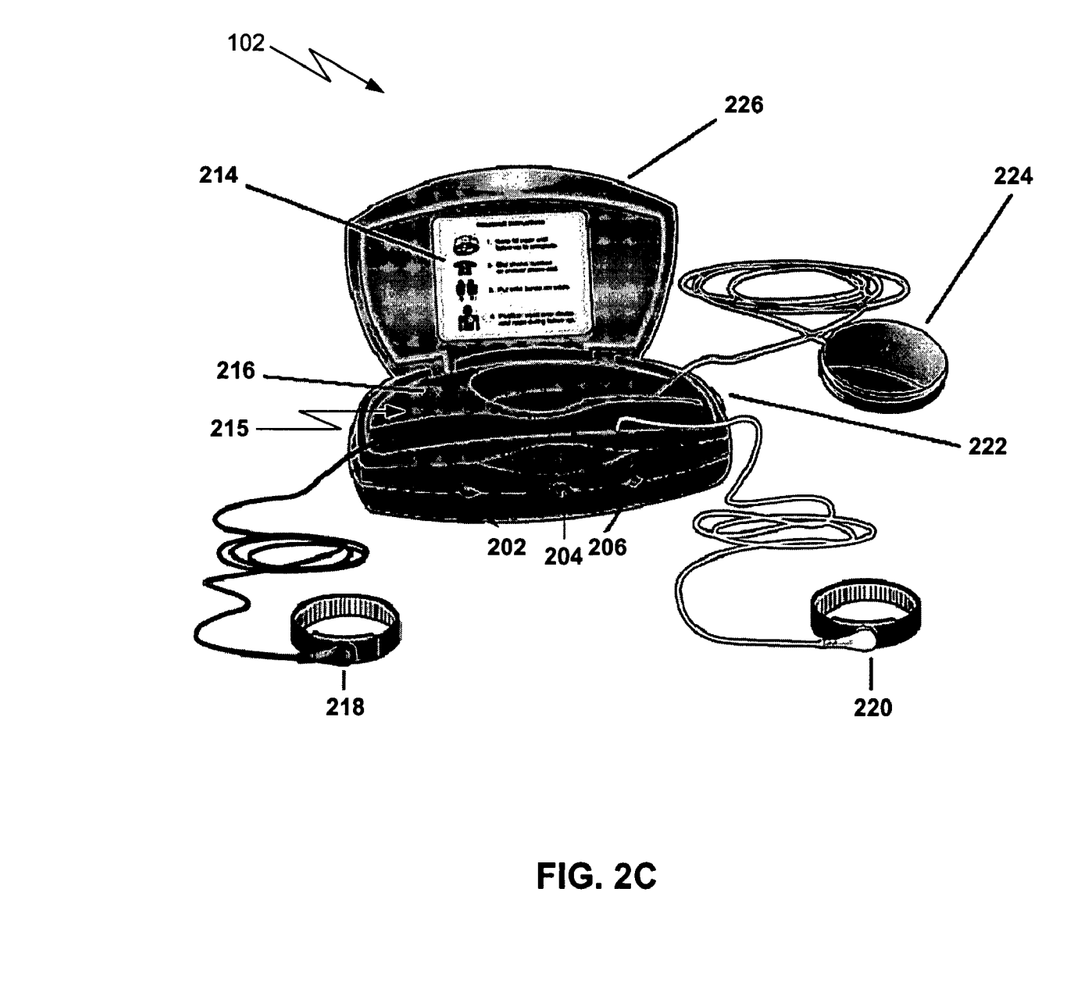
FIG. 2C is an illustration of a third view of the exemplary remote monitoring device.

FIGS. 2A-2C are illustrations of an exemplary remote monitoring device 102. Device 102 includes a lid 226 to house a speakerphone 215, left and right wrist straps 218 and 220, and a wand 224. Wand 224 is placed on the patient to receive data from the patient's IMD. The speakerphone is used to provide audio feedback to the patient and to act as a telephone. The speakerphone includes both a microphone (not shown) and a speaker 216. Instructions 214 are included on the inside portion of lid 226. Light indicators 202, 204, and 206 provide information related to the operation of the remote monitoring device 102 to the patient. Volume control 222 controls the volume of the speaker 216. The remote monitoring device further contains a power supply connection 208, a telephone cord plug 212 for connecting the remote monitoring device 102 to a telephone network and a telephone jack 210 for connecting the remote monitoring device 102 to a telephone.

As would be appreciated by persons skilled in the relevant art, the remote monitoring device 102 shown is provided as an example and other devices for remotely monitoring IMDs may include additional or fewer elements as well as substitute elements. For example, instructions 214 may not be provided, a lid 226 may not be used to house the various components or start a session using the remote monitoring device 102, or a wired or wireless broadband connection may be substituted for the telephone cord plug 212. The exemplary remote monitoring device 102 shown in FIGS. 2A-2C will be used below to further describe a user interface suitable for patients that are visually and/or hearing impaired.

Figure 3:
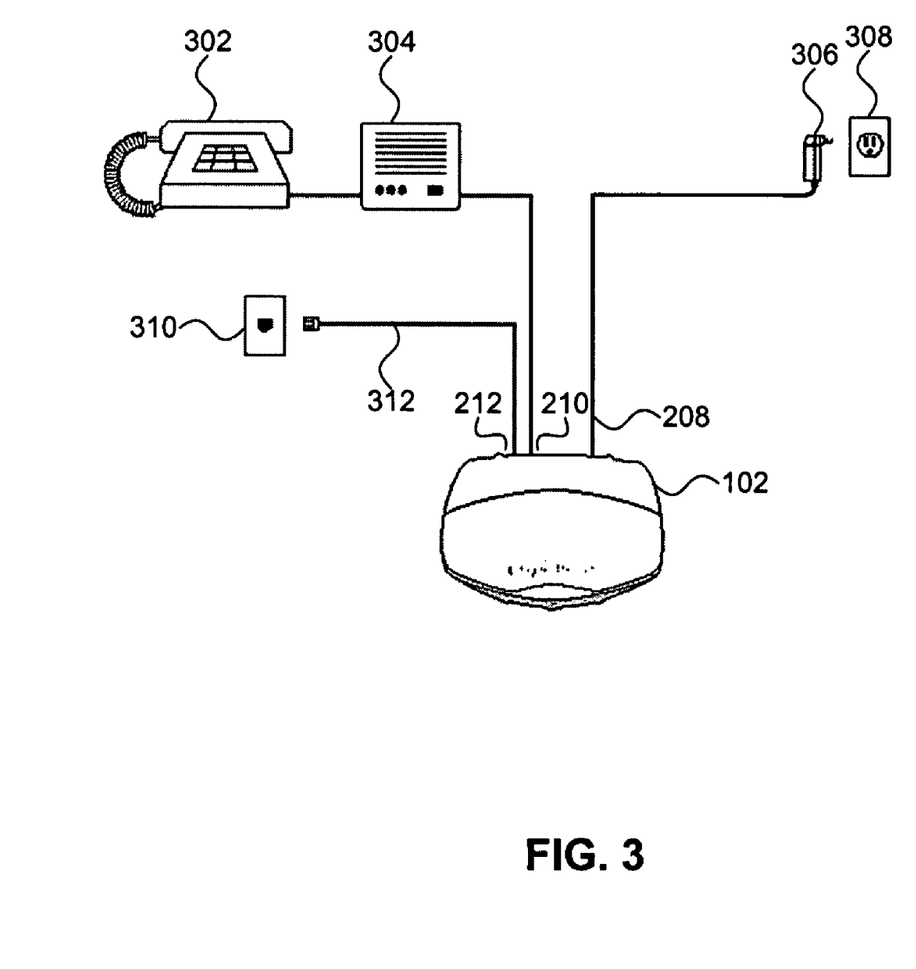
FIG. 3 is a diagram of an exemplary installation of the exemplary remote monitoring device.

FIG. 3 is a diagram of an exemplary installation of the remote monitoring device 102 at a site remote from the medical provider. A power cord 306 is connected between the power supply connection 208 and a wall electrical outlet 308 to provide power to the remote monitoring device 102. A telephone cord is connected between the telephone cord plug 212 and a wall phone jack 310 to provide the remote monitoring device 102 with access to the telephone network. Optionally, a telephone cord 312 is connected from the telephone jack 210 to an answering machine 304 or telephone 302. As would be appreciated by persons skilled in the relevant art, different installations of a remote monitoring device may be required for different configurations of the remote monitoring device.

Figure 4:
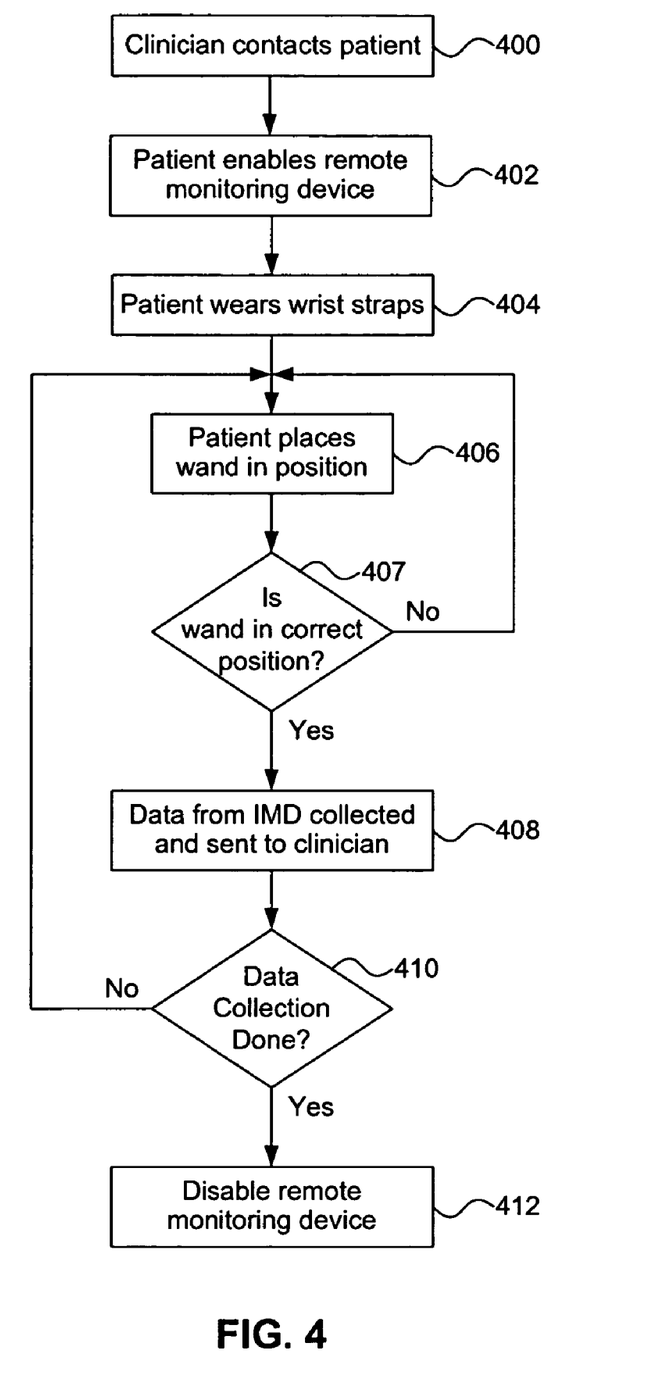
FIG. 4 is a flow chart describing the steps of an exemplary remote follow-up session using the exemplary remote monitoring device.

FIG. 4 is a flow chart describing the steps of an exemplary remote follow-up session using the exemplary remote monitoring device 102. In step 400, a clinician who is at a location remote from the patient contacts the patient to initiate a remote follow-up session. Typically, the clinician initiates the follow-up session by making a telephone call to the patient. The patient may also initiate the follow-up session by calling the clinician.

After the clinician and the patient are in contact, the patient, in step 402, opens the lid 226 on the remote monitoring device 102. Opening the lid 226 activates the remote monitoring device 102 and the power light 202 turns on. At this time and periodically thereafter, if the remote monitoring device 102 detects an internal problem, all of the lights 202, 204, and 206 will blink at the same time and a series of double beeps will be played on the speaker 216 to inform the patient that the remote monitoring device 102 is not functioning properly. If the remote monitoring device 102 is functioning properly when activated, the speakerphone is enabled to allow the patient to speak with the clinician without the use of a telephone handset. Therefore, the patient may hang up any other telephones the patient may have used to communicate with the clinician before enabling the remote monitoring device 102.

In step 404, the patient places the left and right wrist straps 218 and 220 on the patient's wrists. The wrist straps may be used to obtain additional information about the patient during the follow-up session.

In step 406, the clinician instructs the patient to position the wand 224 on the patient's body to receive data from the patient's IMD. The patient may lay down or sit upright and rest the wand 224 on his or her body near the IMD. Wand 224 may be placed on the skin or on top of the patient's clothing. Wand 224 may contain a special coating or a textured surface to facilitate gripping or sticking to the patient's clothing or skin. In step 407, the clinician detects whether the wand is correctly positioned in proximity to the IMD. If not, the patient moves the wand until the correct position is indicated by appropriate lights, sounds or vibrations. When wand 224 is unable to receive data from the IMD, light indicator 206 may go into an ON state or may blink and/or a continuous series of beeps (e.g. three beeps) may be played on the speaker 216 to instruct the patient to reposition the wand 224.

When the patient has positioned the wand 224 properly so that the remote monitoring device 102 can receive data from the IMD, light indicator 206 may go to an OFF state or may stop blinking and remain on and/or a single set of (three) slow beeps may be played on the speaker 216. While the patient positions the wand 224 near the IMD, the clinician is able to hear the beeps played by the remote monitoring device 102 over the speakerphone. Hence, the clinician is able to provide guidance and determine if the patient has properly positioned the wand 224 to receive data from the IMD. Alternatively, the wand 224 may vibrate when it is not positioned properly to receive data from the IMD. At any time during the follow-up session, if the wand 224 becomes displaced or is unable to retrieve data from the IMD, the patient will receive similar light and sound indications as described above to instruct the patient to reposition the wand 224.

Once the wand 224 is in proper position, data from the IMD is collected in step 408. Data collection may be initiated by the clinician, who sends a signal from his or her receiving device 106 to the remote monitoring device 102 to start data collection. Alternatively, remote monitoring device 102 may be configured to allow the patient to initiate the data collection. Once data collection begins, telephone conversation over the speakerphone is disabled to allow the transmission of collected data over the telephone network to a receiving device at the clinician's site. During data collection and transmission, light indicator 206 remains on and a continuous beep at ten second intervals is played on the speaker 216. At any time while the data is being collected, the patient may pick up a telephone handset or a TTY device to communicate with the clinician. In addition, in the event that the clinician wants to communicate with the patient, light indicator 204 will blink and a ringing will be played on the speaker 216 three times to indicate that the patient should pick up his or her telephone handset, use a TTY device, or speak with the clinician over the speakerphone. When the patient and clinician communicate over the telephone, TTY device or speakerphone, data collection is stopped. Data collection may be subsequently resumed.

In step 410, if the clinician indicates over the telephone that the data collection is complete, the patient may finish the follow-up session as described in step 412. Otherwise, steps 406 and 408 may be repeated until data collection is complete.

In step 412, the patient returns the left and right wrist wraps 218 and 220 and the wand 224 to the housing of the remote monitoring device 102 and closes the lid 226 to end the follow-up session. Closing the lid 226 disables the remote monitoring device 102. If after the data collection has been completed and the lid 226 is not closed for an hour, the remote monitoring device 102 may turn itself off.

As described above, the use of lights, sound, vibration, and position of physical components such as the lid 226 provides a user interface that is appropriate for visually and/or hearing impaired patients. Different audio signals are used to distinguish different conditions during the remote follow-up session for visually impaired patients. As would be appreciated by persons skilled in the relevant art, other types of audio indicators may be used instead of beeps to indicate various conditions. For example, music, tones and narratives as well as various combinations, sequences and repetitions of the various audio sounds may be utilized. Different light states are used to distinguish different conditions during the remote follow-up session for hearing impaired patients. As would be appreciated by persons skilled in the relevant art, other types of light states may be used to indicate various conditions. For example, combinations, sequences and repetitions of light flashes may be utilized. Furthermore, tactile features such as the opening of the lid 226 and vibration is useful for both hearing and visually impaired patients. The availability of the speakerphone allows the clinician to hear the remote monitoring device 102 and communicate with the patient when data is not being transmitted. The ability of the remote monitoring device 102 to switch as needed between transmitting data and allowing voice or TTY communication over the telephone network allows the clinician and the patient to stay in close communication during the follow-up session.

Table 1 below highlights the lights and sounds of one exemplary embodiment of the remote monitoring device 102 during a remote follow-up session.

TABLE 1

Remote monitoring device's lights and sounds during follow-up session

| Lights | Sound | What it means | What the patient should do |
| --- | --- | --- | --- |
| Power light 202 . . . OFF<br>Phone light 204 . . . OFF<br>Wand light 206 . . . OFF | No Sound | If the lid 226 is closed, device 102 is not powered on. If the lid 226 is open, device 102 is in standby mode. | If not in use, this is OK. Otherwise the patient should make sure the device is installed properly as in FIG. 3 and make sure the lid 226 is open. |
| Power light 202 . . . ON<br>Phone light 204 . . . OFF<br>Wand light 206 . . . OFF | No Sound | Device 102 is powered on and ready. | Patient should wait for clinician's instructions. |
| Power light 202 . . . ON<br>Phone light 204 . . . OFF<br>Wand light 206 . . . BLINKING | Continuous series of three beeps | Device 102 is trying to locate the IMD. The wand 224 is not in the correct position or has moved out of the correct position. | The patient should move the wand 224 over the patient's IMD. |
| Power light 202 . . . ON<br>Phone light 204 . . . OFF<br>Wand light 206 . . . ON | no sound | Device 102 has located the IMD and the wand 224 is in the correct position. | Patient should wait for clinician's instructions. |
| Power light 202 . . . ON<br>Phone light 204 . . . OFF<br>Wand light 206 . . . ON | Continuous beep at 10 second intervals | Device 102 has located the IMD and is retrieving data. | Data transmission is in progress and patient should wait until the clinician contacts the patient. |
| Power light 202 . . . ON<br>Phone light 204 . . . BLINKING<br>Wand light 206 . . . ON or OFF | Transmitter rings three times | Clinician wants to speak with the patient. | The patient should use the speakerphone or telephone handset to listen to clinician's instructions. |
| Power light 202 . . . BLINKING<br>Phone light 204 . . . BLINKING<br>Wand light 206 . . . BLINKING | Continuous series of double beeps | Device 102 did not pass the self-test or some other type of error occurred while in session. | Patient should unplug the device 102's power cord and plug it in again. If the self-test does not pass or an error occurs again, the patent should contact the clinician. |

Table 2 below describes the light indicator states of another exemplary embodiment of the remote monitoring device 102.

TABLE 2

Remote monitoring device's light indicator states

| Light | Description |
| --- | --- |
| Power light 202 . . . ON | Lid 226 is open. |
| Power light 202 . . . OFF | Lid 226 is closed. |
| Phone light 204 . . . OFF | Nothing requested of patient. |
| Phone light 204. . . BLINKING | Patient requested to pickup phone handset. |
| Wand light 206 . . . OFF | Device 102 is not searching for IMD. |
| Wand light 206 . . . ON | Device 102 located IMD successfully. |

TABLE 2-continued

Remote monitoring device's light indicator states

| Light | Description |
| --- | --- |
| Wand light 206 . . . BLINKING | Device 102 is searching for IMD, wand 224 is out of position. |
| All lights blinking continuously | Device 102 failed self-test on power up. |

Table 3 below describes the audio states of a further exemplary embodiment of the remote monitoring device 102.

TABLE 3

Remote monitoring device's audio states

| Sound | Description |
| --- | --- |
| One beep | Device 102 has been plugged into a power source. |
| One short beep every ten seconds | Device 102 is transmitting data to the clinician. |
| A set of 3 beeps | Wand 224 has successfully located the IMD. |
| A set of 3 short beeps continuously | Wand 224 is out of position. |
| A set of 4 short beeps three times | Device 102 is going to voice mode and activity the speakerphone. The patient may alternatively pickup a telephone handset. |

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

What is claimed is:

1. A device to remotely monitor a patient fitted with an implantable medical device, comprising:
   a communication device configured to permit remote communication with a clinician, the communication device comprising a microphone and a speaker;
   a wand that can be placed on the patient and is capable of receiving data from an implantable medical device in the patient;
   a transceiver by which a clinician can contact the device remotely to obtain data received from the implantable medical device through the wand,
   wherein a first audio state is provided by the speaker when the wand is not positioned properly on the patient to receive data from the implantable medical device,
   wherein a second audio state is provided by the speaker when the wand is positioned properly on the patient to receive data from the implantable medical device,
   wherein the first and second audio states are audible to the clinician over the communication device,
   wherein a third audio state is provided by the speaker when the clinician is receiving the data, and
   wherein a fourth audio state is provided by the speaker when the clinician is not receiving the data.

2. The device of claim 1 further comprising a wrist strap.

3. The device of claim 1 wherein the wand is configured to removeably attach to the patient.

4. The device of claim 3 wherein the wand has a textured surface.

5. The device of claim 3 wherein the wand is coated to facilitate attachment to the patient.

6. The device of claim 1, wherein the audio state comprises silence, a single beep, a sequence of beeps, a repetition of beeps, tones, music, and/or narrative.

7. The device of claim 1, further comprising at least one light indicator, wherein:
   a first light state is provided by the at least one light indicator when the wand is not positioned properly on the patient to receive data from the implantable medical device, and
   a second light state is provided by the at least one light indicator when the wand is positioned properly on the patient to receive data from the implantable medical device.

8. A device to remotely monitor a patient fitted with an implantable medical device, comprising:
   a communication device configured to permit remote communication with a clinician, the communication device comprising a microphone and a speaker;
   a wand that can be placed on the patient and is capable of receiving data from an implantable medical device in the patient;
   wherein a first audio state is provided by the speaker when the wand is not positioned properly on the patient to receive data from the implantable medical device,
   wherein a second audio state is provided by the speaker when the wand is positioned properly on the patient to receive data from the implantable medical device,
   wherein the first and second audio states are audible to the clinician over the communication device,
   wherein a third audio state is provided by the speaker when the clinician requests the patient to communicate with the clinician through the communications device by voice or TTY, and
   wherein a fourth audio state is provided by the speaker when the clinician is not requesting the patient to communicate with the clinician through the communications device by voice or TTY.

9. A device to remotely monitor a patient fitted with an implantable medical device, comprising:
   a communication device configured to permit remote communication with a clinician, the communication device comprising a microphone and a speaker;
   a wand that can be placed on the patient and is capable of receiving data from an implantable medical device in the patient;
   a lid which can be opened and closed;
   wherein a first audio state is provided by the speaker when the wand is not positioned properly on the patient to receive data from the implantable medical device,
   wherein a second audio state is provided by the speaker when the wand is positioned properly on the patient to receive data from the implantable medical device,
   wherein the first and second audio states are audible to the clinician over the communication device,
   wherein one of the opened and closed state of the lid indicates an ON condition, and
   wherein the other of the opened and closed state of the lid indicates an OFF condition.

10. The device of claim 9, wherein a third audio state is provided by the speaker when the wand is not attempting to retrieve data from the implantable medical device, and
   wherein a fourth audio state is provided by the speaker when the wand is retrieving data from the implantable medical device.

11. The device of claim 9 further comprising at least one light indicator, wherein:
   a first light state is provided by the at least one light indicator when the device detects an internal problem, and
   a third audio state is provided by the speaker when the device detects an internal problem.

12. A device to remotely monitor a patient fitted with an implantable medical device, comprising:
   a communication device configured to permit remote communication with a clinician, the communication device comprising a microphone and a speaker;
   a wand that can be placed on the patient and is capable of receiving data from an implantable medical device in the patient;
   at least one light indicator;
      wherein a first audio state is provided by the speaker when the wand is not positioned properly on the patient to receive data from the implantable medical device,
      wherein a second audio state is provided by the speaker when the wand is positioned properly on the patient to receive data from the implantable medical device,
      wherein the first and second audio states are audible to the clinician over the communication device,
      wherein a first light state is provided by the at least one light indicator when the wand is not positioned properly on the patient to receive data from the implantable medical device,
      wherein a second light state is provided by the at least one light indicator when the wand is positioned properly on the patient to receive data from the implantable medical device,
      wherein a third light state is provided by the at least one light indicator when the clinician requests the patient to communicate with the clinician through the communications device by voice or TTY, and
      wherein a fourth light state is provided by the at least one light indicator when the clinician is not requesting the patient to communicate with the clinician through the communications device by voice or TTY.

13. The device of claim 12, wherein the light state comprises ON, OFF, a flash, a sequence of flashes, and/or a repetition of flashes.

14. A device to remotely monitor a patient fitted with an implantable medical device, comprising:
   a communication device configured to permit remote communication with a clinician, the communication device comprising a microphone and a speaker;
   a wand that can be placed on the patient and is capable of receiving data from an implantable medical device in the patient;
   at least one light indicator;
      wherein a first audio state is provided by the speaker when the wand is not positioned properly on the patient to receive data from the implantable medical device,
      wherein a second audio state is provided by the speaker when the wand is positioned properly on the patient to receive data from the implantable medical device,
      wherein the first and second audio states are audible to the clinician over the communication device,
      wherein a first light state is provided by the at least one light indicator when the wand is not positioned properly on the patient to receive data from the implantable medical device,
      wherein a second light state is provided by the at least one light indicator when the wand is positioned properly on the patient to receive data from the implantable medical device,
   wherein a third light state is provided by the at least one light indicator, a third audio state is provided by the at least one speaker, and a vibratory state is provided when the clinician requests the patient to communicate with the clinician through the communication device by voice or TTY.

* * * * *